United States Patent [19]

Mann et al.

[11] Patent Number: 4,723,380
[45] Date of Patent: Feb. 9, 1988

[54] OPHTHALMOLOGIC EXAMINATION UNIT

[75] Inventors: Dieter Mann, Aschaffenburg; Dieter Fornoff, Darmstadt; Andreas Ries, Darmstadt; Eberhard Klett, Darmstadt; Michael Van Suntum, Darmstadt, all of Fed. Rep. of Germany

[73] Assignee: Dieter Mann GmbH, Aschaffenburg, Fed. Rep. of Germany

[21] Appl. No.: 757,798

[22] Filed: Jul. 22, 1985

[30] Foreign Application Priority Data

Jul. 30, 1984 [DE] Fed. Rep. of Germany ....... 3428100

[51] Int. Cl.$^4$ ...................... E04H 1/06; B65G 65/00; A61B 3/00
[52] U.S. Cl. .......................................... 52/29; 901/15; 901/16; 351/245; 74/469
[58] Field of Search .................... 901/15, 16; 351/245; 74/469, 479; 248/286, 287; 52/29

[56] References Cited

U.S. PATENT DOCUMENTS

| 3,434,249 | 3/1969 | Richey | 52/32 |
| 3,572,913 | 3/1971 | Korb et al. | 351/245 |
| 4,095,379 | 6/1978 | Weintraub | 52/236.1 |
| 4,543,033 | 9/1985 | Czermak et al. | 901/16 |
| 4,571,149 | 2/1986 | Soroka et al. | 901/16 |

FOREIGN PATENT DOCUMENTS

| 1294067 | 4/1969 | Fed. Rep. of Germany . |
| 1491046 | 4/1975 | Fed. Rep. of Germany . |
| 3428100 | 2/1986 | Fed. Rep. of Germany ...... 351/245 |

OTHER PUBLICATIONS

Monatsheft fur Feinmechanik und Optik, vol. 79, 1962, J5, pp. 147 and 148.

Primary Examiner—James L. Ridgill, Jr.
Attorney, Agent, or Firm—Donald Brown; Robert T. Gammons

[57] ABSTRACT

An examination unit which is particularly suitable as an ophthalmologic examination unit for the examination of a patient by an ophthalmologist, comprises a storage region for an examination apparatus, wherein the storage region is defined by a wall, and an opening in the wall for passing the examination apparatus therethrough from the storage region. In order to ensure an easy transfer of the examination unit to the patient a support frame is provided in the storage region having a pivot bearing with a pivot axis. A swivel arm is pivotable around the pivot axis from a rest position in which the swivel arm is positioned within the storage region, into an operating position in which the swivel arm has the free end thereof laterally swung out of the storage region through the opening. Furthermore, the examination apparatus is suspended at the free end of the swivel arm.

10 Claims, 7 Drawing Figures

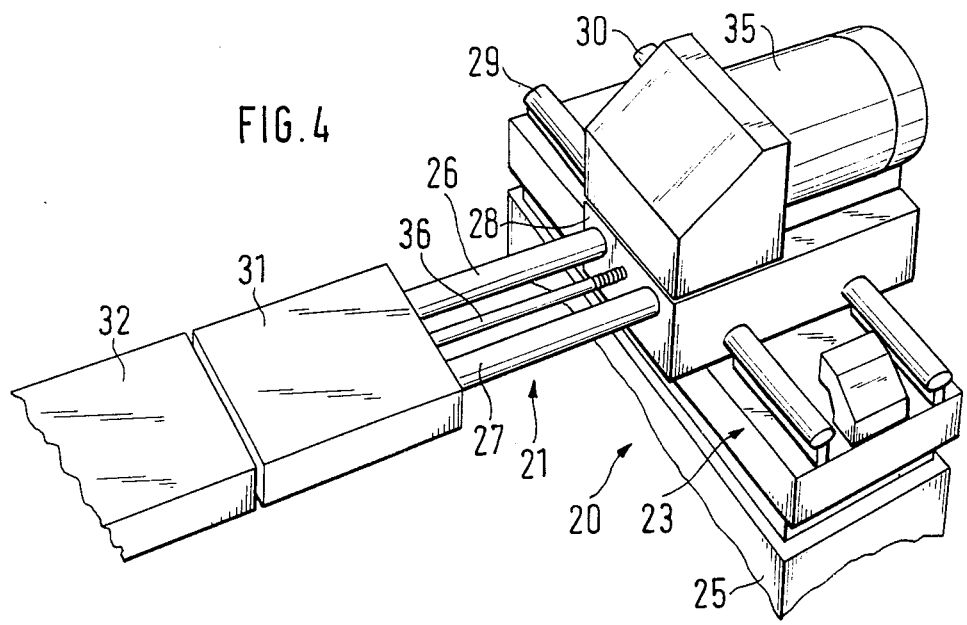
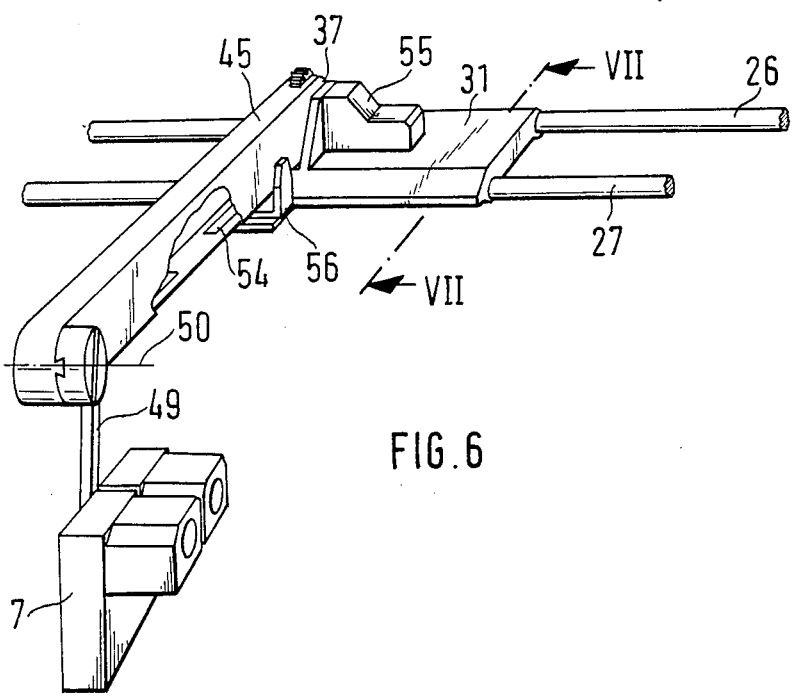

OPHTHALMOLOGIC EXAMINATION UNIT

BACKGROUND OF THE INVENTION

The invention refers to an examination unit comprising a storage region for an examination apparatus, wherein the storage region is defined by a wall, and an opening in the wall for passing the examination apparatus therethrough from the storage region.

An examination unit of this kind which is particularly suitable for use as an ophthalmologic examination unit is disclosed in the U.S. Pat. No. 4,095,379. In this known apparatus a plurality of examination apparatus is disposed at the periphery of a rotary table which is separated from the examination room by a wall. The wall has an opening and the respective desired examination apparatus may be drawn outwards into the examination room on a sliding guide. The examination apparatus stands on a base support which is moved out together with the examination apparatus. This base support may impede the examination of a patient and further represents an instability factor in that the patient may strike the base support and thus adulterate the measurement or the adjustment. Further examination units or supports therefor are disclosed in the German Pat. Nos. 12 94 067 and 14 91 046 as well as in "Monatsheft für Feinmechanik and Optik", Vol. 79, 1962, J. 5, pages 147-148.

OBJECTS OF THE INVENTION

It is the object of the invention to provide an improved examination unit in which the above described drawbacks are avoided. It is a further object of the invention to provide an examination unit allowing an easy transfer of the apparatus from a rest position in which they are stored in a covered manner, into an operating position in which any impediment or impairment of the examination is avoided. It is a still further object of the invention to keep the space required for the storage of the examination apparatus as small as possible. It is a still further object of the invention to provide an examination unit which may be used as ophtalmologic examination unit.

SUMMARY OF THE INVENTION

This object is achieved by an examination unit comprising a storage region for an examination apparatus, wherein the storage region is defined by a wall, and an opening in the wall for passing the examination apparatus therethrough from the storage region, wherein a support frame is provided in the storage region having a pivot bearing with a pivot axis for pivoting a swivel arm therearound from a rest position in which the swivel arm is positioned within the storage region into an operating position in which the swivel arm has its free end laterally swung out of the storage region through the opening, and wherein the examination apparatus is suspended at the free end of the swivel arm.

According to a particularly preferred embodiment of the invention a plurality of examination apparatus, in particular a slit lamp, an ophthalmometer, a refractometer and a phoropter, are disposed at a respective swivel arm one behind the other within the storage region and may individually be swung out through the opening into the treatment region between the doctor and the patient. Hence it is possible to select the respective suitable apparatus out of a plurality of examination apparatus, whereby the other apparatus remain within the storage region which requires only a small space due to the consecutive disposition of the apparatus.

According to a further preferred embodiment the examination unit is mounted as a unit separating two examination rooms and the storage region has a second wall with a second opening on the side of the pivot bearing opposite to the wall. The swivel arm may be pivoted together with the respective examination apparatus through the second opening into the other treatment room. In this manner only one of each of the expensive examination apparatus is required for two examination rooms.

BRIEF DESCRIPTION OF THE DRAWINGS

Further features and advantages of the invention will stand out from the description of an embodiment in connection with the Figures. In the Figures

FIG. 4 is a perspective view of an adjusting means used in the inventive examination unit;

FIG. 6 is a perspective view of the inventive swivel arm; and

Figure 3:
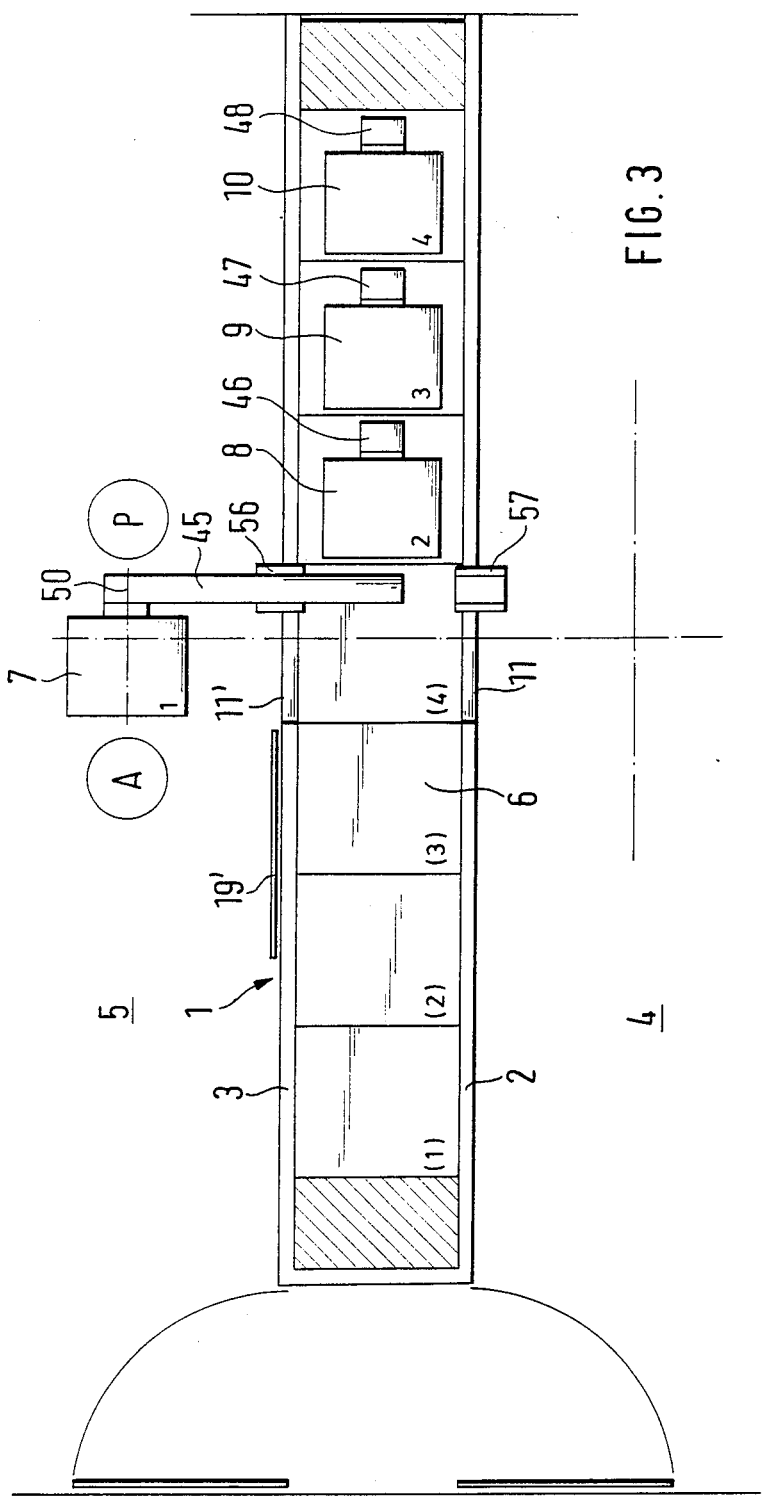
FIG. 3 is a sectional view of the inventive examination unit taken along the line III—III in FIG. 1 in schematic representation with swung out examination unit.

The inventive examination unit 1 comprises, as may in particular be seen from FIG. 3, two substantially parallel walls 2, 3 which together form a separating wall between two treatment rooms 4, 5. The distance between the walls 2, 3 is selected such that a storage region 6 is formed therebetween receiving a plurality of examination apparatus 7, 8, 9, 10 disposed in a line one behind the other. The width of the walls 2, 3 or of the examination unit 1, respectively, is selected such that 2n−1 locations for examination apparatus 7, 8, 9, 10 are provided disposed consecutively in horizontal line in direction of the walls 2, 3, wherein n represents the number of the examination apparatus in question.

Figure 1:
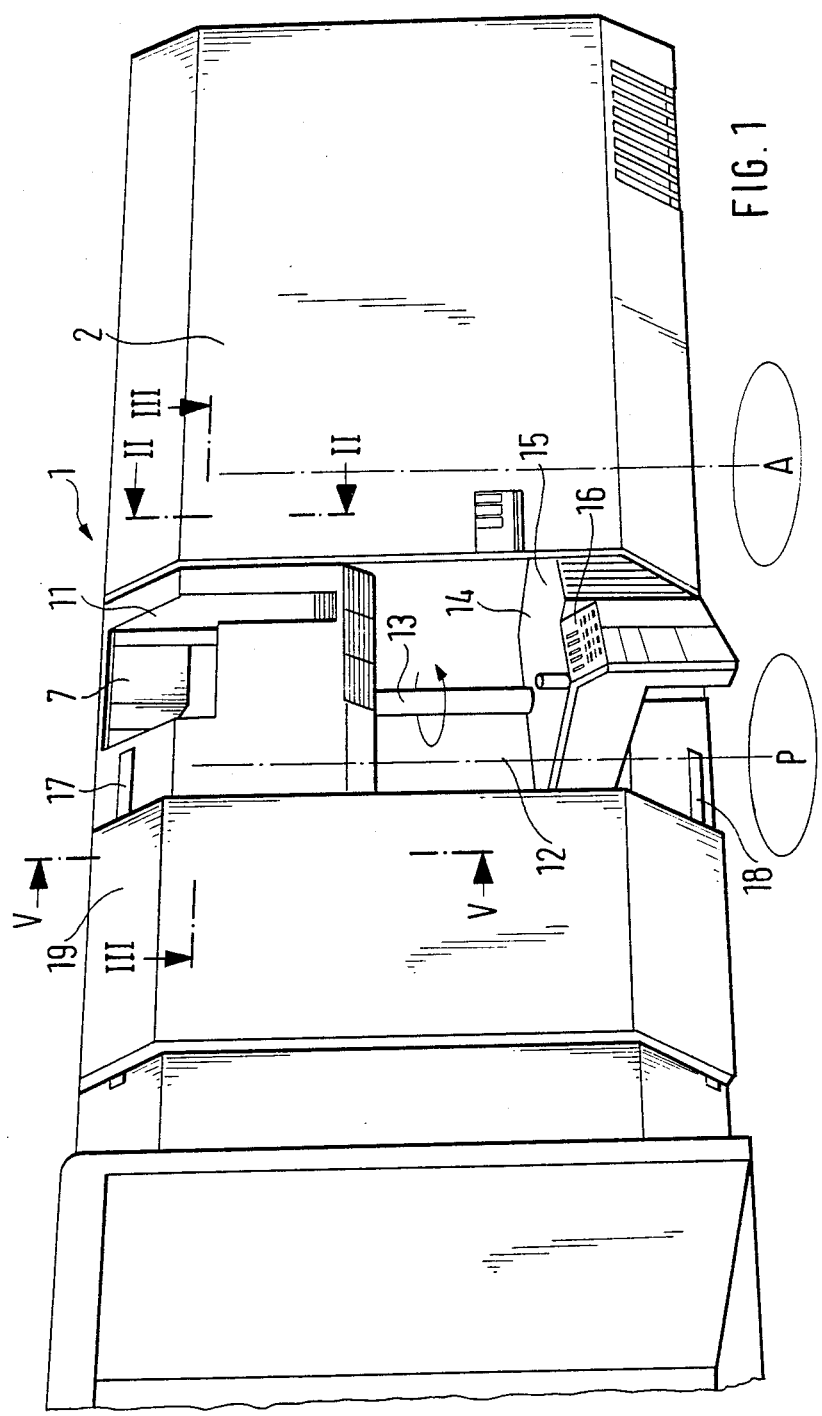
FIG. 1 is a perspective view of an inventive examination unit with opened sliding door.
Figure 5:
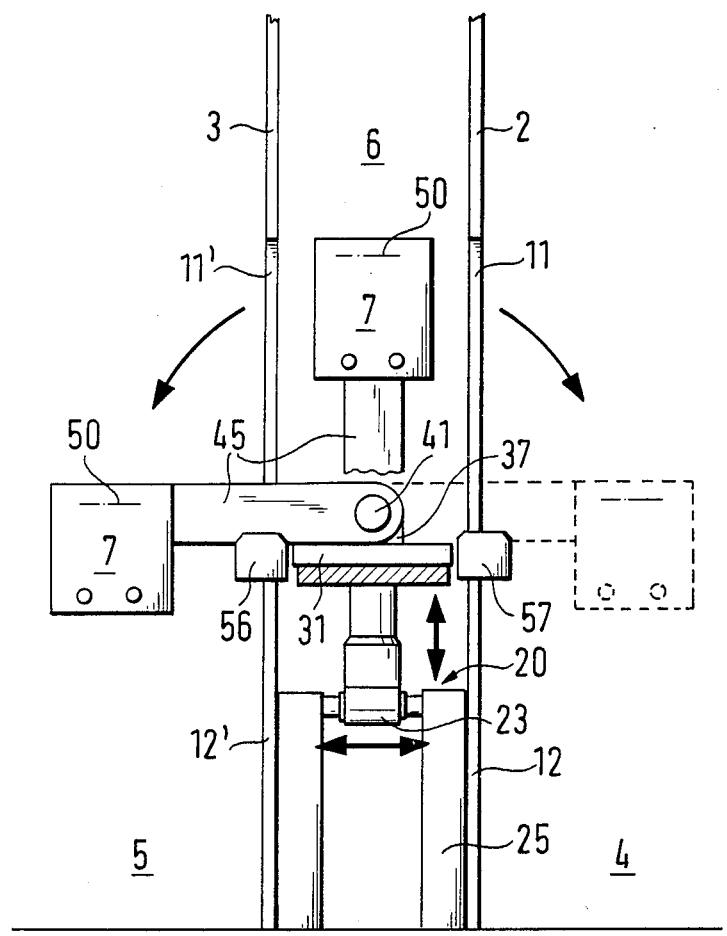
FIG. 5 is a sectional view through the inventive examination unit taken along the line V—V in FIG. 1 in schematic representation.

A respective opening 11, 11' and a recess 12, 12' therebelow is provided at corresponding locations about in the middle of the walls 2, 3 in the manner shown in the FIGS. 1 and 5. The opening 11, 11' is positioned substantially in the upper half of the wall and has a shape such that an examination apparatus may be swung outwards from the storage region 6 through the wall in the manner to be described later on. A control desk 14 being pivotable around vertical axis 13 and having a working area 15 as well as a number of control means 16 formed e.g. as switches and displays for controlling the examination unit is provided within the recess 12, 12'. Moreover, the walls 2, 3 have respective guides 17, 18 for a sliding door 19, 19' covering the corresponding opening 11, 11' and recess 12, 12' in closed position and clearing the same in the opening position on one side of the corresponding opening 11, 11' or recess 12, 12' respectively.

Figure 2:
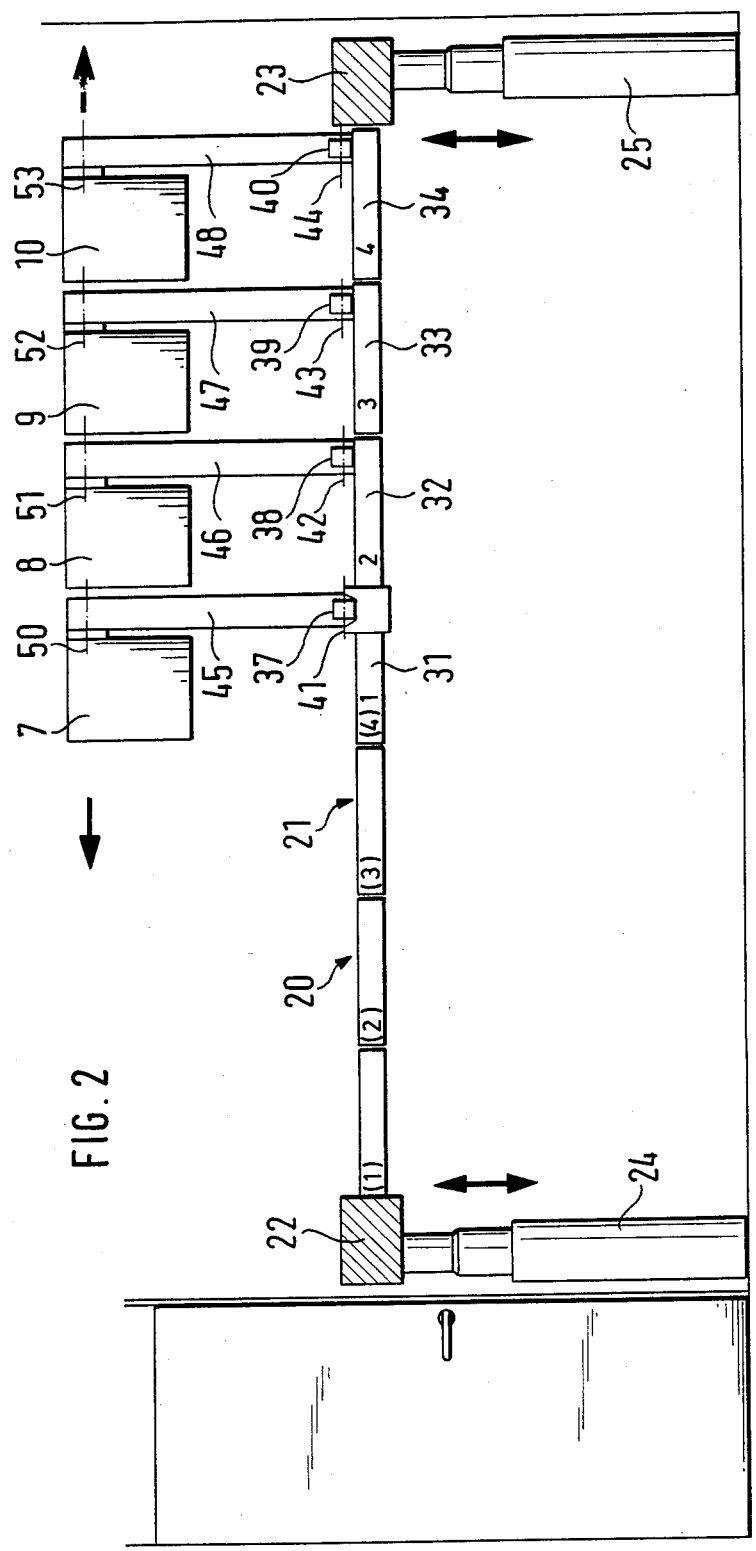
FIG. 2 is a sectional view of the inventive examination unit along the line II—II in FIG. 1 in schematic representation.

The arrangement of the individual examination apparatus 7, 8, 9, 10 may in particular be seen from FIG. 2. To this end a support frame 20 is provided between the walls 2, 3 which comprises a substantially horizontally disposed longitudinal guide 21 in the middle between both walls 2, 3. The longitudinal guide 21 extends over nearly the total width of the walls 2, 3 and has the two ends thereof connected with a respective cross-guide 22, 23 which rest on the floor via a respective foot 24, 25. The length of the feet 24, 25 and hence the elevation of the cross-guides 22, 23 is adjustable by means of a suitable adjustment means, for instance a spindle or hydraulic apparatus.

In the manner shown in particular in FIG. 4 the longitudinal guide 21 has two parallel guide bars 26, 27 having their respective ends supported in a sliding carriage 28. The cross-guides 22, 23 also have two parallel guide bars 29, 30 which are disposed substantially horizontally and transversely to the guide bars 26, 27 and which have the sliding carriage 28 supported thereon in a manner slidable transversely to the walls 2, 3. The sliding carriage 28 is displaced in direction of the guide bars 29, 30 by a spindle drive or rack-and-pinion drive or any other suitable drive.

A plurality of sliding carriages 31, 32, 33, 34 corresponding in number to the examination apparatus 7, 8, 9, 10 to be used is slidably guided on the guide bars 26, 27. The sliding carriages 31, 32, 33, 34 are all connected with each other. For displacing the sliding carriages 31, 32, 33, 34 an electromotive drive 35 is provided which is mounted on the sliding carriage 28 and rotates a spindle 36 disposed between the guide bars 26, 27 and engaging a spindle nut connected with the sliding carriages 31, 32, 33, 34. However, any other suitable drive for displacing the sliding carriages 31, 32, 33, 34, for instance a chain or belt drive or a rack-and-pinion drive, may be used.

The drive of the sliding carriage 28 and the drive 35 of the sliding carriages 31, 32, 33, 34 each has a quick motion gear and a slow motion gear for the quick displacement or exact adjustment, respectively, of the position of the sliding carriages 31, 32, 33, 34 in a horizontal plane.

Thus each of the sliding carriages 31, 32, 33, 34 forms a platform which is displaceable in a substantially horizontal plane and has a respective examination apparatus 7, 8, 9, 10 mounted thereto. The connection of the examination apparatus 7, 8, 9, 10 with the appropriate sliding carriages 31, 32, 33, 34 may in particular be seen from the FIGS. 2, 5 and 6.

A respective pivot bearing 37, 38, 39, 40 having a pivot axis 41 being substantially horizontal and central between the two walls 2, 3 is disposed on the top side of each sliding carriage 31, 32, 33, 34. A respective end of a swivel arm 45, 46, 47, 48 is supported in each pivot bearing 37, 38, 39, 40 in a manner to be pivotable in a plane perpendicular to the pivot axis 41, 42, 43, 44 and transversely to the walls 2, 3. A respective examination apparatus 7, 8, 9, 10 is suspended at the other free end of each swivel arm 45, 46, 47, 48 via a connection 49 having one end mounted to the examination apparatus 7, 8, 9, 10 close to or at the top side thereof and the other end mounted to the free end of the swivel arm 45, 46, 47, 48 in a manner to be pivotable around an axis 50, 51, 52, 53 parallel to the pivot axis 41, 42, 43, 44. In this manner the examination apparatus 7, 8, 9, 10 remains in an upright operating position independent of the position of the swivel arm 45, 46, 47, 48 merely due to the action of gravity. However, this may positively be achieved according to the embodiment shown in FIG. 4 by forming the swivel arm 45, 46, 47, 48 as a parallelogram, where a vertical position of the connection 49 or the examination apparatus 7, 8, 9, 10, respectively, is achieved by means of a belt 54 acting as parallelogram and disposed in the interior of the swivel arms 45, 46, 47, 48.

Figure 7:
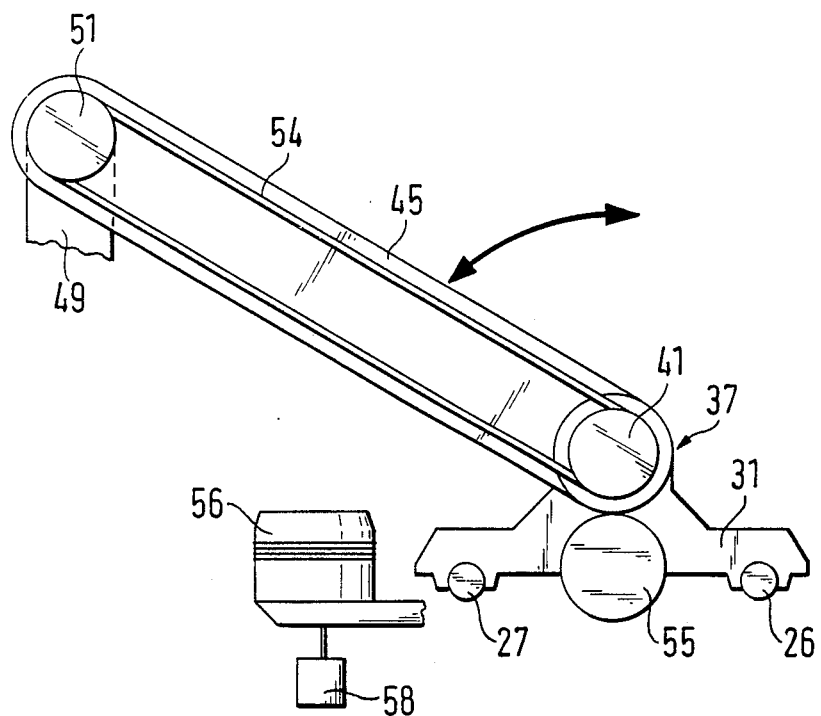
FIG. 7 is a sectional view through the inventive swivel arm taken along the line VII—VII in FIG. 6.

A pivot drive 55 schematically represented in FIG. 6 and mounted on the respective sliding carriage 37, 38, 39, 40 is provided for pivoting the swivel arms 45, 46, 47, 48. The pivot range of the swivel arms 45, 46, 47, 48 extends from a rest position in which the swivel arm 45, 46, 47, 48 stands upright from the respective pivot axis 41, 42, 43, 44 in the manner which may in particular be seen from the FIGS. 2 and 5, symmetrically on both sides of this rest position as far as a substantially horizontal operating position shown in the FIGS. 5 and 6. Stops 56, 57 formed as U-shaped supporting parts for supporting the respective swivel arm 45, 46, 47, 48 in the both end positions thereof are mounted at the sliding carriage 31, 32, 33, 34 on both sides of the pivot axis 41, 42, 43, 44. The position of the stops 56, 57 and the elevation of the longitudinal guide 21 of the support frame 20 is selected such that the respective swivel arm 45, 46, 47, 48 is about in a horizontal position whenever the examination apparatus 7, 8, 9, 10 mounted thereto is positioned in operating position, i.e. about in eye level of a patient sitting on a chair in front of the examination unit. For adaption to the size of the patient an elevation adjustment 58 having a quick motion gear for elevation adjustment of the eye level of the examination apparatus 7, 8, 9, 10 between 1100 and 1350 mm, preferably between 1175 mm and 1275 mm, and a slow motion gear for elevation adjustment by 15 mm for fine adjustment is provided which is schematically indicated in FIG. 7.

In operation the examination unit is first opened on the side of the room in which the examination will take place. To this end the respective sliding door 19, 19' is laterally displaced along the guides 17, 18 by push-button control or the like so that the sliding door clears the opening 11 or 11', respectively, and the recess 12 or 12', respectively. Thereupon the control desk 14 may be pivoted out of the recess 12 towards the doctor's position A so that the working area 15 and the control means 16 may be accessed.

Now the examinating doctor selects the suitable examination apparatus 7, 8, 9, 10 via the control means 16. As a consequence the drive 35 moves the coherent sliding carriages 31, 32, 33, 34 until the sliding carriage with the requested examination apparatus 7, 8, 9, 10 has a position adjacent to the opening 11, 11' such that the examination apparatus 7, 8, 9, 10 may be swung outwardly out of the opening 11 together with the respective swivel arm 45, 46, 47, 48. Thereupon the pivot drive 55 is operated by further push-button control or automatically and pivots the swivel arm 45, 46, 47, 48 on the side of the respective cleared opening 11, 11' laterally outwards from the vertical rest position until it abuts the respective stop 56, 57 and rests thereon. Thus the examination apparatus 7, 8, 9, 10 is in an operating position between the patient indicated P in FIG. 1 and the doctor A.

Thereupon the examination apparatus 7, 8, 9, 10 is adjusted. To this end first the elevation adjustment 58 is operated via the control means and thereby the swivel arm 45, 46, 47, 48 is brought into such a position that the examination apparatus 7, 8, 9, 10 is exactly in the required elevation. Thereupon a slow motion gear of the drive 35 is switched on if required, in order to perform a fine adjustment of the distance between the examination apparatus 7, 8, 9, 10 and the eye. To this end the travel of the sliding carriage 31, 32, 33, 34 for displacement by the slow motion gear is about between 30 and 100 mm and preferably about 65 mm. Finally, the sliding carriage 28 is displaced by means of a further command signal inputted via the control means 16 until the examination apparatus 7, 8, 9, 10 is adjusted to one eye of the patient. This exact adjustment is preferably again made by a slow motion gear with an adjustment travel distance of about 10-20 mm and preferably 15 mm, wheras the displacement from one eye to the other is made by a quick motion gear. The total lateral displacement distance of the sliding carriage 28 and hence of the examination apparatus 7, 8, 9, 10 is between 40 and 100 mm and preferably between 52 and 80 mm corresponding to the distance of the pupils.

In case that the examination is to be continued with a different examination apparatus 7, 8, 9, 10 the examination apparatus 7, 8, 9, 10 used is pivoted back into the rest position within the storage region 6 by means of a control signal inputted via the control means 16 and the desired new examination apparatus is brought into the operation position in the above described manner. At the end of the examination the last used examination apparatus is swung back into the rest position, the control desk 14 is pivoted back from the operation position thereof turned towards the doctor and the sliding door 19, 19' is closed. Hence the operation apparatus 7, 8, 9, 10 as well as the control desk 14 are accomodated in a dust-proof manner.

For the examination apparatus in particular four devices are used namely slit lamp, ophtalmometer, refractometer and phoropter. By admitting the devices from above a large usable space results in the lower region of the unit 1 which besides of the control desk may be used for handy placing of further diagnosis accessories such as glass boxes etc. The control desk 14 may be a switch board or a computer terminal with keyboard.

Although the invention has been described with reference to specific example embodiments, it is to be understood that it is intended to cover all modifications and equivalents within the scope of the appended claims.

What is claimed is:

1. an examination unit comprising an examination apparatus, a storage space for storing said examination apparatus in an inoperative position and support means for supporting said examination apparatus within said storage space and for moving said examination apparatus from within said storage space to an operative position externally of the storage space; said storage space comprising a vertically-disposed wall defining at least one side of the storage space, said wall having an opening therein through which said examination apparatus can be moved from within the storage space to said operative position externally of said storage space and support means comprising a support structure within said storage space, a pivot bearing mounted to the support means, said pivot bearing having a substantially horizontal pivot axis parallel to the side wall, said support means further comprising a swivel arm pivotally mounted at one end thereof to said pivot bearing and means suspending said examination apparatus at the other end of said swivel arm whereby said examination apparatus may be moved from said inoperative position within the storage space through said opening in said wall into said operative position outside of said storage space by swinging said swivel arm in a substantially vertical plane around said pivot axis from a substantially vertical position within the storage space to a substantially horizontal position exteriorly of said storage space.

2. The examination unit of claim 1 wherein said wall comprises a recess below said pivot axis for receiving a control unit.

3. The examination unit of claim 1 wherein said storage space is defined by a second wall having an opening and being disposed on the side of said pivot bearing opposite to said first wall at a distance which is less than the length of said swivel arm, whereby the distal end of said swivel arm from which said examination apparatus is suspended may be moved outwards from said storage space through said opening in said second wall.

4. The examination unit of claim 1 wherein said support means comprises means for displacing said pivot bearing in a first direction substantially perpendicular to said wall and first drive means for displacing said pivot bearing in said first direction.

5. The examination unit of claim 4 wherein said support means comprises means for slidably displacing said pivot bearing in a second direction substantially parallel to said wall and perpendicular to said pivot axis, and a second drive means for displacing said pivot bearing in said second direction.

6. The examination unit of claim 1 comprising a stop for supporting said swivel arm in said substantially horizontal position thereof, said stop being provided in a lateral distance from said pivot axis which is smaller than the length of said swivel arm.

7. The examination unit of claim 6 comprising means for adjusting the elevation of said stop.

8. The examination unit of claim 1 comprising a plurality of examination apparatus, swivel arms disposed one behind the other in the direction of said pivot axis, and guide means for slidably supporting each swivel arm in the direction of said pivot axis into a position in which it may be pivoted through said opening.

9. The examination unit of claim 8 wherein said guide means comprises a sliding carriage mounting said pivot bearing, a carriage guide guiding said sliding carriage and extending in the direction of said pivot axis, and a carriage drive for moving said sliding carriage.

10. The examination unit of claim 9 wherein said sliding carriages are connected with each other, said carriage drive jointly driving said sliding carriages.

* * * * *